US006248777B1

United States Patent
Koga et al.

(10) Patent No.: US 6,248,777 B1
(45) Date of Patent: Jun. 19, 2001

(54) REMEDIES FOR PERIPHERAL CIRCULATION DISTURBANCES

(75) Inventors: Hiroshi Koga, Tokyo; Hisanori Takanashi; Eiji Kumagai, both of Shizuoka-ken, all of (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/380,376

(22) PCT Filed: Mar. 2, 1998

(86) PCT No.: PCT/JP98/00849

§ 371 Date: Apr. 21, 2000

§ 102(e) Date: Apr. 21, 2000

(87) PCT Pub. No.: WO98/38992

PCT Pub. Date: Sep. 11, 1998

(30) Foreign Application Priority Data

Mar. 3, 1997 (JP) .................................................. 9-048196

(51) Int. Cl.⁷ .......................... A61K 31/35; C07D 311/04
(52) U.S. Cl. ................................. 514/456; 549/405
(58) Field of Search ........................... 549/405; 514/456, 514/230.5; 546/90

(56) References Cited

U.S. PATENT DOCUMENTS

| | | |
|---|---|---|
| 5,104,890 | 4/1992 | Shiokawa et al. . |
| 5,412,117 | 5/1995 | Koga et al. . |
| 5,447,943 | 9/1995 | Lochead et al. . |
| 5,646,308 | 7/1997 | Koga et al. . |

FOREIGN PATENT DOCUMENTS

| | | |
|---|---|---|
| 0 314 446 | 5/1989 | (EP) . |
| 0 376 524 | 7/1990 | (EP) . |
| 0 389 861 A | 10/1990 | (EP) . |
| 0 398 665 | 11/1990 | (EP) . |
| 0 529 654 A | 3/1993 | (EP) . |
| 0 655 448 | 5/1995 | (EP) . |
| 0 702 952 | 3/1996 | (EP) . |

OTHER PUBLICATIONS

Angersbach, Dieter et al., "Enhancement of muscle blood cell flux and pO2 by cromakalim (BRL 34915) and other compounds enhancing membrane K+conductance, but not by Ca2+antagonists or hydralazine, in an animal model of occlusive arterial disease.", Arch. of Pharma., vol. 337, pp. 341–346 (1988).

Cook, Nigel S. et al., "Therapeutic potential of potassium channel openers in peripheral vascular disease and asthma.", Cardio. Vasc. Drugs and Ther., vol. 7, pp. 555–563 (1993).

Cook, Nigel S. et al., "Effects of the potassium channel openers SDZ–PCO 400 and cromakalim in an in vivo rat model of occlusive arterial disease assessed by P–NMR spectroscopy.", Jour. Vasc. Med. and Bio., vol. 4, No. 1, pp. 14–22 (1993).

Ashwood, Valerie A. et al., "Synthesis and antihypertensive activity of 4–(Cyclic amido)–2H–1–benzopyrans.", J. Med. Chem., vol. 29, pp. 2194–2201 (1986).

Patent Abstracts of Japan; vol. 1995, No. 10, (JP 07 188210 A, Jul. 25, 1995); Nov. 30, 1995.

*Primary Examiner*—Deborah C. Lambkin
(74) *Attorney, Agent, or Firm*—Browdy and Neimark

(57) ABSTRACT

It is an object of the present invention to provide novel therapeutic agents for peripheral vascular disease.

The present invention provides pharmaceutical compositions comprising a benzopyran or benzoxazine derivative of the general formula (1):

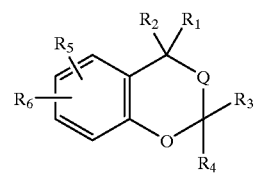

wherein;

$R_1$ represents a hydrogen atom, a lower alkyl group or an aryl group, or $R_1$ directly couples with Q or $R_{11}$ to form a single bond;

$R_2$ represents a substituted or unsubstituted amino group, a saturated or unsaturated heterocyclic group, A—O— or —C(=X)Y;

Q represents =N—, $N^+$—$O^-$ or $C(R_{11})R_{12}$;

$R_3$ and $R_4$ each represent a hydrogen atom, a lower alkyl group or a substituted lower alkyl group having a halogen atom or a lower alkoxy group as a substituent or the like; and $R_5$ and $R_6$ each represent a hydrogen atom, a halogen atom, a lower alkyl group, a lower haloalkyl group or the like; and a pharmaceutically acceptable carrier.

7 Claims, No Drawings

REMEDIES FOR PERIPHERAL CIRCULATION DISTURBANCES

This application is a 371 of PCT/JP98/00849 Mar. 2, 1998.

FIELD OF THE INVENTION

The present invention relates to therapeutic agents for peripheral vascular disease, comprising a benzopyran or benzoxazine derivative having a therapeutic effect for peripheral vascular disease as an active ingredient.

BACKGROUND ART

Peripheral vascular diseases are broadly classified into Buerger's disease and arterioscleorosis obliterans (ASO). In Japan, the former had previously prevailed, but the latter rapidly increased with an increase of arteriosclerotic diseases and the proportion between both was reversed about 20 years ago. Recent reports say that ASO occupies 80% or more of peripheral vascular disease. ASO is a disease which induces atherosclerotic lesion mainly in extremital aortae, resulting in stenosis or occlusion with ischemic condition. Arteriosclerosis often occurs in leg-governing arteries extending from subrenal aorta to femoral arteries among systemic vessels, so that ASO is one of the most frequent diseases in advancing society.

Most of ASO patients basically have arteriosclerosis. Therefore, ASO therapy involves not only improvement of peripheral vascular disease but also correction of risk factors of arteriosclerosis. Important risk factors of ASO are similar to those of other arteriscleroses, such as male, aging, smoking, hypertension, hyperlipemia, diabetes, etc. particularly smoking, hyperlipemia (especially, low HDL and high neutral fats) and diabetes. In-cases complicated with diabetes, peripheral vessels are more likely to occlude to invite more severe condition leading to leg amputation.

Subjective symptoms of leg circulatory disorders vary with the severity of disorders in the leg. Early mild cases show little symptoms only with occasional "cold feeling or numbness", but-advanced cases (medium illness) show "intermittent claudication" with pain in leg muscles during walking, and more advanced circulatory disorders (severe illness) hamper bloodstream in legs even at rest to invite "pain at rest, gangrene or ulceration". Many cases showing pain-at rest, gangrene or ulceration have too complex arterial lesions to treat so that it is not unusual to resort to leg amputation. If such diseases could be diagnosed earlier and appropriately treated at earlier stages, the improvement of QOL (quality of life) of patients would be promoted.

Therapeutic guidelines for ASO have proposed correction of risk factors of arteriosclerosis (quitting the habit of smoking, diet therapy, exercise, and therapy with hypolipemic agents, antihypertensive agents or hypoglycemic agents) and therapy with internal medicines for mild illness; injection, catherterization (PTA) and surgical therapy in addition to said therapies for medium illness; and surgical therapy for severe illness (when it is inadaptable, intravenous injection or arterial injection).

The primary object of pharmacotherapy for ASO is to ensure bloodstream to affected limbs. In order to increase local bloodstream, it is important to enlarge vessels at that site and to enhance the rheology of blood at the same time. Currently commercialized or developed drugs are classified into two major groups according to these purposes. Namely, they are peripheral vasodilators and blood rheology promoters (including platelet aggregation inhibitors and anticoagulants), that are used alone or in combination. They are administered orally or via injection (intravenous injection or arterial injection), particularly via injection in medium or more severe cases with strong subjective symptoms.

Currently used oral drugs include cilostazol having a vasodilative effect as well as an antiplatelet effect (commercial name: Pletaal), prostaglandin (PG) preparations (commercial names: Dorner, Opalmon, etc.), ticlopidine mainly having an antiplatelet effect (commercial name: Panaldine), sarpogrelate (commercial name: Anplag) and ethyl icosapentate (commercial name: Epadel) which is also adaptable to hyperlipemia. They have different action mechanisms, so that it may be required to use two or three preparations in combination depending on pathology. Particularly in medium illness, multiple drugs are more likely to be applied. Injectable preparations include prostaglandin $E_1$ preparations, antithrombin preparations (commercial name: Argatroban), etc. They are in principle used for medium or more severe illness requiring hospitalization.

The efficacy of the existing drugs is not wholly satisfactory. Particularly, antiplatelets such as ticlopidine or ethyl icosapentate are less effective, probably because it is unclear to which extent platelets are involved in each pathology, or whether the vasodilative effect is sufficient even if a drug has such an effect, or whether bloodstream at ischemic sites can be selectively enough ensured. As to bloodstream at ischemic sites, steal phenomenon has been reported with PG preparations, i.e. bloodstream at ischemic sites rather decreased in about 20% of patients particularly treated via injection. This means that pharmacotherapy with PG injection may rather deteriorate pathology.

DISCLOSURE OF THE INVENTION

It is an object of the present invention to provide novel therapeutic agents for peripheral vascular disease.

As a result of careful studies of therapeutic agents for peripheral vascular disease, we accomplished the present invention on the basis of the finding that compounds of the following general formula (1) have excellent effects of improving peripheral vascular disease.

Accordingly, the present invention provides pharmaceutical compositions comprising a benzopyran or benzoxazine derivative of the general formula (1):

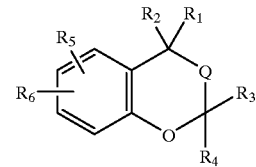

(1)

wherein:

$R_1$ represents a hydrogen atom, a lower alkyl group or an aryl group, or $R_1$ directly couples with Q or $R_{11}$ to form a single bond;

$R_2$ represents a substituted or unsubstituted amino group, a saturated or unsaturated heterocyclic group, A—O— wherein A represents a saturated or unsaturated carbocyclic group or a saturated or unsaturated heterocyclic group, or —C(=X)Y wherein X represents O, S, N—Z or CHNO2 with Z denoting a hydrogen atom, a lower alkyl group, an aryl group, a hydroxyl group, a lower alkoxy group, a cyano group, a carbamoyl group or a sulfamoyl group, and Y represents —NR₇R₈, —OR₉ or —SR₁₀ wherein R₇ and R₈ are identical or different and each represent a hydrogen atom, a hydroxyl group, a lower alkoxy group, a cyano group, a substituted or unsubstituted amino group, a substituted or unsubstituted and saturated or unsaturated aliphatic hydrocarbon group, a substituted or unsubstituted aryl group, or a substituted or unsubstituted heteroaryl group, or R₇ and R₈ are joined together to form an optionally substituted heterocycle with a nitrogen atom, and R₉ and R₁₀ each represent a hydrogen atom, a lower alkyl group or an aryl group;

Q represents =N—, N⁺—O⁻or C(R₁₁)R₁₂ wherein R₁₁ and R₁₂ are identical or different and each represent a hydrogen atom, a hydroxyl group or a lower acyloxy group, or R₁₁ directly couples with R₁ to form a single bond, or R₁₁ and R₁₂ are joined together to form =O;

R₃ and R₄ are identical or different and each represent a hydrogen atom, a lower alkyl group or a substituted lower alkyl group having a halogen atom or a lower alkoxy group as a substituent, or R₃ and R₄ are joined together to represent a polymethylene group, or R₃ and R₄ are joined together to represent a heterocycle having an oxygen atom or a sulfur atom as a heteroatom; and R₅ and R₆ are identical or different and each represent a hydrogen atom, a halogen atom, a lower alkyl group, a lower haloalkyl group, a lower alkoxy group, a lower haloalkoxy group, an amino group, an acylamino group, a nitro group, a cyano group, an ester group, a lower alkylsulfonyl group or an arylsulfonyl group, or R₅ and R₆ are joined together to represent =N—O—N=; and a pharmaceutically acceptable carrier.

Preferably, the present invention provides pharmaceutical compositions comprising a benzopyran derivative of the general formula (2):

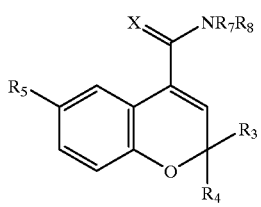

(2)

wherein:

R₃ and R₄ are identical or different and each represent a lower alkyl group or a substituted lower alkyl group having a halogen atom or a lower alkoxy group as a substituent;

R₅ represents a hydrogen atom, a halogen atom, a lower alkyl group, a lower haloalkyl group, a lower alkoxy group, a lower haloalkoxy group, an amino group, an acylamino group, a nitro group, a cyano group, an ester group, a lower alkylsulfonyl group or an arylsulfonyl group;

X represents O or S; and

R₇ and R₈ are identical or different and each represent a hydrogen atom, a hydroxyl group, a lower alkoxy group, a cyano group, a substituted or unsubstituted amino group, a substituted or unsubstituted and saturated or unsaturated aliphatic hydrocarbon group, a substituted or unsubstituted aryl group, or a substituted or unsubstituted heteroaryl group, or R₇ and R₈ are joined together to form an optionally substituted heterocycle with a nitrogen atom; and a pharmaceutically acceptable carrier.

In the above general formula (2), it is preferred that R₅ represents a lower haloalkyl group and/or R₇ and R₈ are identical or different and each represent a substituted or unsubstituted and saturated or unsaturated aliphatic hydrocarbon group.

More preferably, the present invention provides pharmaceutical compositions comprising a benzopyran derivative of the general formula (3):

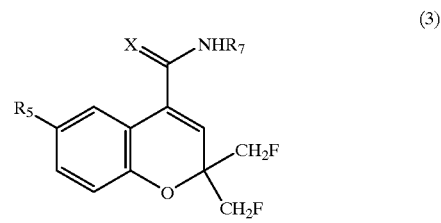

(3)

wherein:

R₅ represents a hydrogen atom, a halogen atom, a lower alkyl group, a lower haloalkyl group, a lower alkoxy group, a lower haloalkoxy group, an amino group, an acylamino group, a nitro group, a cyano group, an ester group, a lower alkylsulfonyl group or an arylsulfonyl group;

X represents O or S; and

R₇ represents a substituted lower alkyl group; and a pharmaceutically acceptable carrier.

In the above general formula (3), R₅ preferably represents a lower haloalkyl group.

Still more preferably, the present invention provides pharmaceutical compositions comprising a benzopyran derivative of the general formula (4):

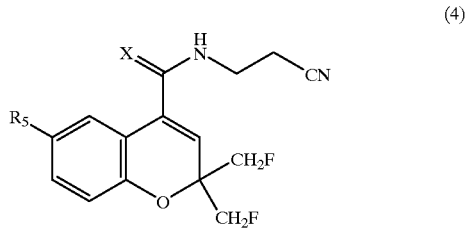

(4)

wherein R₅ represents a lower haloalkyl group, and X represents O or S;

and a pharmaceutically acceptable carrier.

Especially preferably, the present invention provides pharmaceutical compositions comprising one or more benzopyran derivatives selected from the group consisting of:

N-(2-cyanoethyl)-6-pentafluoroethyl-2,2-bisfluoromethyl-2H-1-benzopyran-4-carbamide;

N-(2-cyanoethyl)-6-pentafluoroethyl-2,2-bisfluoromethyl-2H-1-benzopyran-4-carbothioamide;

N-(2-cyanoethyl)-2,2-bisfluoromethyl-6-trifluoromethyl-2H-1-benzopyran-4-carbothioamide;

N-(2-cyanoethyl)-2,2-bisfluoromethyl-6-trifluoromethyl-2H-1-benzopyran-4-carbamide;

N-(2-cyanoethyl)-2.2-bisfluoromethyl-6-heptafluoropropyl-2H-1-benzopyran-4-carbamide; and N-(2-cyanoethyl)-2,2-bisfluoromethyl-6-heptafluoropropyl-2H-1-benzopyran-4-carbothioamide;

and a pharmaceutically acceptable carrier.

Most preferably, the present invention provides pharmaceutical compositions comprising N-(2-cyanoethyl)-6-pentafluoroethyl-2,2-bisfluoromethyl-2H-1-benzopyran-4-carbamide and a pharmaceutically acceptable carrier.

Pharmaceutical compositions of the present invention can be used as therapeutic agents for peripheral vascular disease.

According to another aspect of the present invention, a method for treating peripheral vascular disease is provided, said method comprising administering a pharmaceutical composition comprising a therapeutically effective amount of a benzopyran or benzoxazine derivative of the general formula (1):

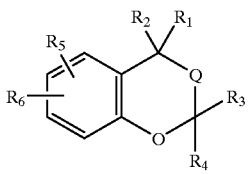
(1)

wherein $R_1$ to $R_6$ and Q are as defined above, and a pharmaceutically acceptable carrier to a patient in need of such a treatment.

Preferred embodiments of the benzopyran or benzoxazine derivative of the general formula (1) used in the method for treating peripheral vascular disease according to the present invention are as described above for pharmaceutical compositions of the present invention.

According to still another aspect of the present invention, a use of a benzopyran or benzoxazine derivative of the general formula (1):

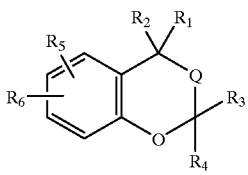
(1)

wherein $R_1$ to $R_6$ and Q are as defined above, for the preparation of a therapeutic agent for peripheral vascular disease is provided.

Preferred embodiments of the benzopyran or benzoxazine derivative of the general formula (1) used for the preparation of a therapeutic agent for peripheral vascular disease according to the present invention are as described above for pharmaceutical compositions of the present invention.

Compounds of the above general formula (1) as well as sub-general formulae (2), (3) and (4) are known compounds, as disclosed in International Publications WO92/14439, WO93/15068, WO94/04521 and WO94/25021, for example. The disclosures of these publications are incorporated herein by reference in their entirety.

It has previously been reported, for example in the above International Publications, that compounds of the above general formula (1) have a potassium channel opening effect, and therefore they are effective for use as smooth muscle relaxants such as antasthmatic agents, antihypertensive agents, antianginal agents or therapeutic agents for urinary incontinence, or for use as hair generation promoters. However, it has not been reported but now first found by us that said compounds have the effect of improving peripheral vascular disease.

THE MOST PREFERRED MODE FOR CARRYING OUT THE INVENTION

As used herein, the term "lower alkyl group" means a straight or branched alkyl group generally containing 1 to 6, preferably 1 to 4 carbon atoms. Examples of such a lower alkyl group include methyl, ethyl, n-propyl, i-propyl, n-butyl, i-butyl, s-butyl, t-butyl.

As used herein, the term "aryl group" means a group obtained by removing a hydrogen atom from an aromatic hydrocarbon. The aryl group may contain any number of carbon atoms, but generally 6 to 22, preferably 6 to 14 carbon atoms. Specific examples of the aryl group include phenyl, tolyl, xylyl, biphenyl; naphthyl, anthryl, phenanthryl, especially preferably phenyl.

As used herein, substituents on the amino group include, for example, a lower alkyl group, a lower alkanoyl group, a lower alkoxy group, a hydroxyl group which may be protected, etc.

As used herein, heterocyclic groups may be saturated or unsaturated monocycles or fused cycles containing any kind of heteroatoms, generally an oxygen, nitrogen or sulfur atom. Heterocyclic groups include, for example, 5- or 6-membered aromatic monoheterocycles containing one O, S or N; 5- or 6-membered saturated monoheterocycles containing one N; 5-membered aromatic monoheterocycles containing each one of O or S and N; 6-membered saturated monoheterocycles containing each one of O or S and N; 5- or 6-membered saturated monoheterocycles containing 2 Ns; 5-membered aromatic monoheterocycles containing 2 or 3 Ns; 6-membered aromatic monoheterocycles containing 2 Ns; 6-membered aromatic monoheterocycles containing 3 Ns. Example of heterocyclic groups include pyrrolidinyl, piperidinyl, pyridyl, pyridazinyl, isoindolyl, 2-oxo-1-pyrrolidinyl, 2-oxo-1-piperidinyl, 2-oxopyridil, 2-thioxo-1-pyridyl, 2-cyanoimino-1,2-dihydro-1-pyridyl.

As used herein, saturated or unsaturated carbocyclic groups may contain any number of carbon atoms, generally 1 to 12, preferably 1 to 8 carbon atoms, and include cyclopropyl, cyclobutyl, cyclopentyl, cyclohexyl, cycloheptyl, cyclooctyl, cyclopentenyl, cyclohexenyl, cyclohexadienyl, cycloheptenyl, cycloheptadienyl, cyclooctenyl, cyclooctadienyl.

As used herein, the term "lower alkoxy group" means an alkoxy group generally containing 1 to 6, preferably 1 to 4 carbon atoms. Specific examples of the lower alkoxy group include, for example, methoxy, ethoxy, n-propoxy, i-propoxy, n-butoxy, i-butoxy, s-butoxy, t-butoxy.

As used herein, saturated or unsaturated aliphatic hydrocarbon groups may be straight, branched or cyclic. Examples of saturated groups include lower alkyl and cycloalkyl groups, and examples of unsaturated groups include lower alkenyl and lower alkynyl groups. The position and number of unsaturated bonds in unsaturated groups are not specifically limited.

The term "cycloalkyl group" means a cycloalkyl group preferably containing 3 to 8 carbon atoms, such as cyclopropyl, cyclobutyl, cyclopentyl, cyclohexyl.

The terms "lower alkenyl group" and "lower alkynyl group" mean straight or branched alkenyl and alkynyl groups generally containing 2 to 6 carbon atoms. The position and nature of unsaturated bonds such as double bond and triple bond are not specifically limited. Examples of lower alkenyl and lower alkynyl groups include, vinyl, allyl, butenyl, pentenyl, hexenyl, ethynyl, propynyl, butynyl, pentynyl.

Aliphatic hydrocarbon groups may be substituted by a substituent such as hydroxyl, alkoxy, aryloxy, amino, alkylamino, arylamino, acylamino, alkylthio, arylthio, nitro, cyano, ester, alkylsulfonyl, arylsulfonyl, carbamoyl, carboxyl, aryl, heteroaryl, acyl.

As used herein, substituents on aryl groups, heteroaryl groups and heterocyclic groups include, for example, alkyl, haloalkyl, hydroxyl, alkoxy, haloalkoxy, aryloxy, amino, alkylamino, arylamino, acylamino, alkylthio, arylthio, nitro, cyano, acyl, carboxyl, ester, carbamoyl, alkylsulfonyl, arylsulfonyl, sulfamoyl.

As used herein, the term "lower acyloxy group" means, for example, acetyloxy, propionyloxy, butylyloxy, valeryloxy.

As used herein, the term "halogen atom" means chlorine, fluorine, bromine or iodine, preferably chlorine and fluorine.

As used herein, the terms "lower haloalkyl group" and "lower haloalkoxy group" mean groups in which the alkyl moiety generally contains 1 to 6, preferably 1 to 4 carbon atoms and "halo" has the same meaning as defined above for halogen atom.

As used herein, the term "acylamino group" means to include, for example, lower alkylcarbonylamino groups such as acetylamino, propionylamino, butyrylamino, and valerylamino.

As used herein, the term "ester group" means to include, for example, lower alkyl ester groups such as methyl ester, ethyl ester, propyl ester, and butyl ester.

As described above, all the compounds of the general formula (1) and sub-general formulae (2) to (4) defined herein are known compounds which can be prepared according to the procedures described in International Publications WO92/14439, WO93/15068, WO94/04521 and WO94/25021 mentioned above.

The amount of a benzopyran or benzoxazine derivative in therapeutic agents for peripheral vascular disease of the present invention is generally in the range from 0.01 to 50% by weight, preferably 0.1 to 10% by weight.

The dosage of therapeutic agents for peripheral vascular disease of the present invention is generally in the range from 0.0001 to 1 mg/kg/day, preferably 0.0005 to 0.1 mg/kg/day expressed as active ingredients.

As used herein, the term "pharmaceutically acceptable carrier" means a carrier that can be routinely used for formulating pharmaceuticals.

The dosage form of therapeutic agents for peripheral vascular disease of the present invention includes tablets, granules, parvules, powders, pills, capsules, troches, solutions, emulsions, suspensions, percutaneous formulations, ointments, lotions, lyophilized formulations, etc.

The administration route can be selected from oral, parenteral, local or other routes, as desired.

The disclosure of the specification of Japanese Patent Application No. 48196/97 on which is based the present application to claim Convention priority is incorporated herein by reference in its entirety.

The following preparation examples and test examples further illustrate the present invention without, however, limiting the same thereto.

EXAMPLES

Preparation Example 1

Preparation of N-(2-cyanoethyl)-2.2-bisfluoromethyl-6-trifluoromethyl-2H-1-benzopyran-4-carbamide (1) To a mixture of 4.05 g of 2,2-bisfluoromethyl-3,4-dihydro-6-nitro-2H-1-benzopyran-4-one and 10 ml of dry benzene were added 2.52 ml of trimethylsilyl cyanide and 0.82 g of zinc iodide with stirring under ice-cooling, and the mixture was stirred at room temperature for 12 hours. The mixture was further combined with 8 ml of pyridine and 4.41 ml of phosphorus oxychloride and heated to reflux for 6 hours. The reaction mixture was acidified with ice water and aqueous hydrochloric acid and extracted with methylene chloride. The organic layer was washed with water and dried, then concentrated under reduced pressure, and the resulting residue was subjected to silica gel column chromatography (eluent; methylene chloride:hexane=7:3) to give 0.99 g of 2,2-bisfluoromethyl-6-nitro-2H-1-benzopyran-4-carbonitrile; m.p. 136–137° C.;

$H^1$-NMR (CDCl$_3$) δ: 4.59 (4H, d), 6.53 (1H, s), 7.03 (1H, d), 8.10–8.40 (2H, m);

MS: 266 (M$^+$).

(2) A mixture of 0.93 g of 2,2-bisfluoromethyl-6-nitro-2H-1-benzopyran-4-carbonitrile, 20 ml of acetic acid, 10 ml of water and 10 ml of sulfuric acid was heated to reflux for 4.5 hours. The reaction mixture was poured Into ice water and the precipitated crystals were filtered off to give 0.83 g of 2,2-bisfluoromethyl-6-nitro-2H-1-benzopyran-4-carboxylic acid; m.p. 171–172° C.;

IR (KBr) cm$^{-1}$=1698 (C=O);

MS: 285 (M$^+$).

(3) A mixture of 41.7 g of 2,2-bisfluoromethyl-6-nitro-2H-1-benzopyran-4-carboxylic acid, 20 ml of sulfuric acid and 300 ml of ethyl alcohol was heated to reflux for 6 hours. The reaction mixture was poured into ice water and the precipitated crystals were filtered off to give 42.7 g of 2,2-bisfluoromethyl-6-nitro-2H-1-benzopyran-4-carboxylic acid ethyl ester; m.p. 96–98° C.;

$H^1$-NMR (CDCl$_3$) δ: 1.42 (3H, t), 4.38 (2H, q), 4.58 (4H, d), 6.69 (1H, s), 6.94 (1H, d), 8.07 (1H, dd), 8.92 (1H, d);

MS: 313 (M$^+$).

(4) A mixture of 42.0 g of 2,2-bisfluoromethyl-6-nitro-2H-1-benzopyran-4-carboxylic acid ethyl ester, 88 g of stannous chloride and 500 ml of ethyl alcohol was heated to reflux for 2 hours. The reaction mixture was combined with an aqueous 2N sodium chloride solution and extracted with ethyl acetate. The organic layer was washed with saturated saline, then dried over sodium sulfate and concentrated under reduced pressure to give 5.2 g of 6-amino-2,2-bisfluoromethyl-2H-1-benzopyran-4-carboxylic acid ethyl ester as an oil;

$H^1$-NMR (CDCl$_3$) δ: 1.31(3H, t), 3.0–4.0 (2H, m), 4.36 (2H, q), 4.55 (4H, d), 6.2–6.9 (3H, m), 7.26 (1H, d);

MS: 283 (M$^+$).

(5) To a mixture of 4.0 g of 6-amino-2,2-bisfluoromethyl-2H-1-benzopyran-4-carboxylic acid ethyl ester, 1.66 g of sulfuric acid and 40 ml of water was added a mixture of 1.09 g of sodium nitrite, 10 ml of methylene chloride and 10 ml of water with ice-cooling, and the reaction mixture was stirred with ice-cooling for 10 minutes. The reaction mixture was further combined with a mixture of 2.85 g of potassium iodide and 5 ml of water and stirred at room temperature for 1.5 hours. The reaction mixture was combined with water and extracted with methylene chloride. The organic layer was washed with an aqueous 20% sodium sulfite solution and saturated saline, then dried over sodium sulfate and concentrated under reduced pressure, and the resulting residue was subjected to silica gel column chromatography (eluent; ethyl acetate:hexane=1:1) to give 3.67 g of 2,2-bisfluoromethyl-6-iodo-2H-1-benzopyran-4-carboxylic acid ethyl ester; m.p. 89–90° C.;

$H^1$-NMR (CDCl$_3$) δ: 1.39 (3H, t), 4.33 (2H, q), 4.58 (4H, d), 6.60 (1H, s), 6.67 (1H, d), 7.02 (1H, dd), 8.30 (1H, d);

MS: 394 (M$^+$).

(6) A mixture of 1.00 g of 2,2-bisfluoromethyl-6-iodo-2H-1-benzopyran-4-carboxylic acid ethyl ester, 0.84 g of potassium trifluoroacetate, 1.18 g of cuprous iodide, 4 ml of toluene and 10 ml of N,N-dimethylformamide was stirred with heating at 150° C. for 5.5 hours under a nitrogen gas atmosphere while removing toluene. The reaction mixture was combined with a mixture of 2N hydrochloric acid and ethyl acetate, and unsoluble matters were filtered out with Celite. Organic layers were collected from the filtrate and the aqueous layer was extracted with ethyl acetate. The organic layers were combined and washed with saturated saline, dried over sodium sulfate, then concentrated under reduced pressure, and the resulting residue was subjected to silica gel chromatography (eluent: ethyl acetate:hexane= 10:1) to give 0.51 g of 2,2-bisfluoromethyl-6-trifluoromethyl-2H-1-benzopyran-4-carboxylic acid ethyl ester as an oil;

$H^1$-NMR (CDCl$_3$) δ: 1.36 (3H, t), 4.31 (2H, q), 4.53 (4H, d), 6.63 (1H, s), 6.94 (1H, d), 7.47 (1H, dd), 8.31 (1H, d);

MS: 336 (M$^+$).

(7) A mixture of 0.51 g of 2,2-bisfluoromethyl-6-trifluoromethyl-2H-1-benzopyran-4-carboxylic acid ethyl ester, 0.13 g of potassium hydroxide and 10 ml of ethyl alcohol was stirred at room temperature for 2 hours. The reaction mixture was combined with ice water and hydrochloric acid, and the precipitated crystals were filtered off to give 0.43 g of 2,2-bisfluoromethyl-6-trifluoromethyl-2H-1-benzopyran-4-carboxylic acid; m.p. 162–163° C.;

$H^1$-NMR (CDCl$_3$) δ: 4.60 (4H, d), 6.69 (1H, s), 7.00 (1H, d), 7.45 (1H, dd), 8.30 (1H, d);

MS: 308 (M$^+$).

(8) A mixture of 0.20 g of 2,2-bisfluoromethyl-6-trifluoromethyl-2H-1-benzopyran-4-carboxylic acid, 0.12 g of N,N-carbonyl diimidazole and 3 ml of tetrahydrofuran was stirred at room temperature for one hour. The reaction mixture was combined with 0.06 g of 2-cyanoethylamine and further stirred at room temperature for 14 hours. The reaction mixture was concentrated under reduced pressure and the resulting residue was subjected to silica gel column chromatography (eluent; ethyl acetate:hexane=1:1) to give 0.20 g of N-(2-cyanoethyl)-2,2-bisfluoromethyl-6-trifluoromethyl-2H-1-benzopyran-4-carbamide; m.p. 135–136° C.

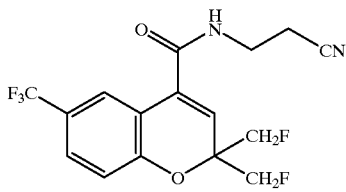

Preparation Example 1

$H^1$-NMR (CDCl$_3$) δ: 2.70 (2H, t), 3.63 (2H, q), 4.57 (4H, d), 6.08 (1H, s), 6.5–7.3 (1H. m), 6.98 (1H, d), 7.50 (1H, dd), 7.84 (1H, d);

MS: 360 (M$^+$).

Preparation Example 2
Preparation of N-(2-cyanoethyl)-2.2-bisfluoromethyl-6-trifluoromethyl-2H-1-benzopyran-4-carbothioamide A mixture of 92 mg of N-(2-cyanoethyl)-2,2-bisfluoromethyl-6-trifluorometyl-2H-1-benzopyran-4-carbamide, 60 mg of Lawesson's reagent and 2 ml of benzene was stirred with heating at 80° C. for one hour. The reaction mixture was subjected to silica gel column chromatography (eluent:methylene chloride) to give 50 mg of N-(2-cyanoethyl)-2,2-bisfluoromethyl-6-trifluoromethyl-2H-1-benzopyran-4-carbothioamide; m.p. 105–106° C.

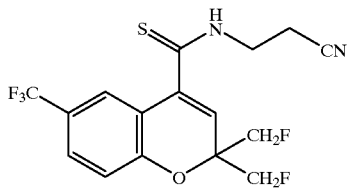

Preparation Example 2

$H^1$-NMR (CDCl$_3$) δ: 2.89 (t, 2H), 4.03 (q, 2H), 4.60 (d, 4H), 5.87 (s, 1H), 7.02 (d, 1H), 7.51 (dd, 1H), 7.82 (d, 1H), 8.10–8.70 (brs, 1H);

MS: 376 (M$^+$).

Preparation Example 3
Preparation of N-(2-cyanoethyl)-6-pentafluoroethyl-2.2-bisfluoromethyl-2H-1-benzopyran-4-carbamide (1) The procedure of Preparation Example 1 (6) was repeated using 2,2-bisfluoromethyl-6-iodo-2H-1-benzopyran-4-carboxylic acid ethyl ester, potassium pentafluoropropionate, cuprous iodide, toluene and N,N-dimethylformamide to give 6-pentafluoroethyl-2,2-bisfluoromethyl-2H-1-benzopyran-4-carboxylic acid ethyl ester as an oil;

$H^1$-NMR (CDCl$_3$) δ: 1.40 (3H, t), 4.38 (2H, q), 4.60 (4H, d), 6.69 (1H, s), 7.00 (1H, d), 7.45 (1H, dd), 8.30 (1H, d);

MS: 386 (M$^+$).

(2) The procedure of Preparation Example 1 (7) was repeated using 6-pentafluoroethyl-2,2-bisfluoromethyl-2H-1-benzopyran-4-carboxylic acid ethyl ester to give 6-pentafluoroethyl-2,2-bisfluoromethyl-2H-1-benzopyran-4-carboxylic acid; m.p. 173–174° C.;

$H^1$-NMR (CDCl$_3$) δ: 4.60 (2H, d), 6.69 (1H, s), 7.00 (1H, d), 7.45 (1H, dd), 8.30 (1H, d);

MS: 358 (M$^+$).

(3) The procedure of Preparation Example 1 (8) was repeated using 6-pentafluoroethyl-2,2-bisfluoromethyl-2H-1-benzopyran-4-carboxylic acid to give N-(2-cyanoethyl)-6-pentafluoroethyl-2,2-bisfluoromethyl-2H-1-benzopyran-4-carbamide; m.p. 144–145° C.

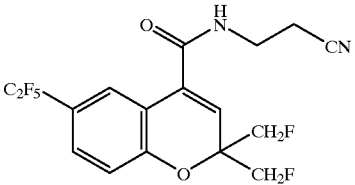

Preparation Example 3

$H^1$-NMR (CDCl$_3$) δ: 2.72 (2H, t), 3.65 (2H, q), 4.60 (4H, d), 6.09 (1H, s), 6.5–7.3 (1H, m), 7.02 (1H, d), 7.52 (1H, dd), 7.83 (1H, d);

MS: 410 (M$^+$).

Preparation Example 4
Preparation of N-(2-cyanoethyl)-6-pentafluoroethyl-2.2-bisfluoromethyl-2H-1-benzopyran-4-carbothioamide The procedure of Preparation Example 2 was repeated using N-(2-cyanoethyl)-6-pentafluoroethyl-2,2-bisfluoromethyl-2H-1-benzopyran-4-carbamide to give N-(2-cyanoethyl)-6-pentafluoroethyl-2,2-bisfluoromethyl-2H-1-benzopyran-4-carbothioamide; m.p. 108–109° C.

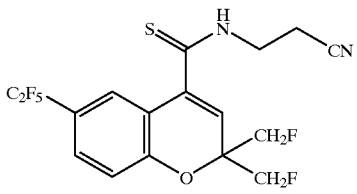

Preparation Example 4

H$^1$-NMR (CDCl$_3$) δ: 2.89 (2H, t), 4.04 (2H, q), 4.57 (4H, d), 5.84 (1H, s), 7.00 (1H, d), 7.46 (1H, dd), 7.64 (1H, d), 7.90–8.40 (brs, 1H);

MS: 426 (M$^+$).

Preparation Example 5
Preparation of N-(2-cyanoethyl)-2.2-bisfluoromethyl-6-heptafluoropropyl-2H-1-benzopyran-4-carbamide (1) The procedure of Preparation Example 1 (6) was repeated using 2,2-bisfluoromethyl-6-iodo-2H-1-benzopyran-4-carboxylic acid ethyl ester, potassium heptafluorobutyrate, cuprous iodide, toluene and N,N-dimethylformamide to give 2,2-bisfluoromethyl-6-heptafluoropropyl-2H-1-benzopyran-4-carboxylic acid ethyl ester as an oil;

H$^1$-NMR (CDCl$_3$) δ: 1.36 (3H, t), 4.32 (2H, q), 4.57 (4H, d), 6.69 (1H, s), 7.02 (1H, d), 7.46 (1H, dd), 8.29 (1H, d);

MS: 436 (M$^+$).

(2) The procedure of Preparation Example 1 (7) was repeated using 2,2-bisfluoromethyl-6-heptafluoropropyl-2H-1-benzopyran-4-carboxylic acid ethyl ester to give 2,2-bisfluoromethyl-6-heptafluoropropyl-2H-1-benzopyran-4-carboxylic acid; m.p. 162–163° C;

H$^1$-NMR (CDCl$_3$) δ: 4.60 (4H, d), 6.69 (1H, s), 7.00 (1H, d), 7.45 (1H, dd), 8.30 (1H, d);

MS: 408 (M$^+$).

(3) The procedure of Preparation Example 1 (8) was repeated using 2,2-bisfluoromethyl-6-heptafluoropropyl-2H-1-benzopyran-4-carboxylic acid to give N-(2-cyanoethyl)-2,2-bisfluoromethyl-6-heptafluoropropyl-2H-1-benzopyran-4-carbamide; m.p. 135–136° C.

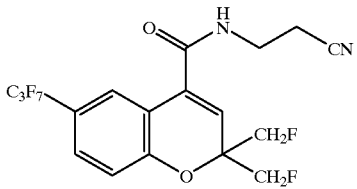

Preparation Example 5

H$^1$-NMR (CDCl$_3$) δ: 2.70 (2H, t), 3.62 (2H, q), 4.58 (4H, d), 6.05 (1H, s), 6.5–7.3 (1H, m), 6.98 (1H, d), 7.43 (1H, dd), 7.78 (1H, d);

MS: 460 (M$^+$).

Preparation Example 6
Preparation of N-(2-cyanoethyl)-2.2-bisfluoromethyl-6-heptafluoropropyl-2H-1-benzopyran-4-carbothioamide The procedure of Preparation Example 2 was repeated using N-(2-cyanoethyl)-2,2-bisfluoromethyl-6-heptafluoropropyl-2H-1-benzopyran-4-carbamide to give N-(2-cyanoethyl)-2,2-bisfluoromethyl-6-heptafluoropropyl-2H-1-benzopyran-4-carbothioamide; m.p. 94–95° C.

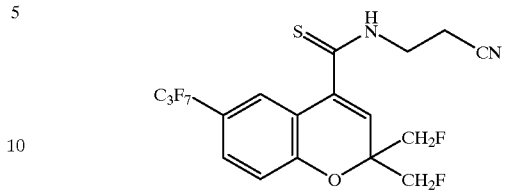

Preparation Example 6

H$^1$-NMR (CDCl$_3$) δ: 2.85 (2H, t), 3.95 (2H, q), 4.51 (4H, d), 5.78 (1H, s), 6.92 (1H, d), 7.47 (1H, dd), 7.56 (1H, d), 7.90–8.40 (brs, 1H);

MS: 476 (M$^+$).

Test Example

Effects of a test compound (N-(2-cyanoethyl)-6-pentafluoroethyl-2.2-bisfluoromethyl-2H-1-benzopyran-4-carbamide hereinafter referred to as KC-515) in model rats of adrenaline/ergotamine-induced peripheral vascular disease (1) Materials and Methods Forty 7-week-old male SD rats (Slc: SD Nippon SLC) were used as test animals.

Experimental groups each consisting of 10 animals were treated with 1 ml/head of vehicle (0.3% CMC solution; control) or a preparation of the test compound (100 μg/kg of KC-515), a low dose of cilostazol (10 mg/kg of cilostazol) or a high dose of cilostazol (30 mg/kg of cilostazol) dissolved in a 0.3% CMC solution.

The test method was according to the procedure described in Kitagawa et al. (Effects of Prostaglandin E$_1$ Derivative, OP-1206 α-Cyclodextrin Inclusion Compound (OP-1206 α-CD) on Rat Peripheral Vascular Disease Models: Gendai Iryo, 18 (additional edition) 2:1–11 (1986)). Each animal was fixed on a rat fixer and 0.1 mg of adrenaline (Bosmin injection: Daiichi Pharmaceutical Co., Ltd.) was divided into two portions and subcutaneously administered to two sites 6 cm distant from the tail end. At the same time, 5 mg/kg of ergotamine (ergotamine tartrate: Tokyo Kasei Kogyo Co., Ltd.) was subcutaneously administered on the dorsum.

The first dosage was given before modeling, and from the following day, each preparation was daily administered once a day up to a total of 14 dosages. Each preparation as compulsorily administered into the stomach with an oral sonde.

The length of sloughing lesion of the tail was measured by reference to marks painted with a felt pen at distances of 5, 10 and 15 cm from the end. Evaluation was made on the day subsequent to completion of 14 dosages. The severity of the lesion was evaluated by measuring the sloughing length plus the length of necrosis over the whole circumference of the tail. Mummified tail ends were also considered as sloughing. Data analyses were according to Dunnett's multiple comparison.

(2) Results

The results obtained are shown in the following Table 1.

TABLE 1

Length of necrosis or sloughing of the tail after administration of test compound (KC-515) or cilostazol for 14 days (mean ± S.E.)

| | Sloughing | Necrosis over the whole circumference | Sloughing + necrosis | Dunnett TEST (T value) |
|---|---|---|---|---|
| Vehicle(n = 9) | 7.67 ± 0.80 cm | 1.61 ± 0.22 cm | 9.28 ± 0.79 cm | |
| Cilostazol 10 mg(n = 10) | 7.75 ± 0.37 cm | 1.60 ± 0.23 cm | 9.35 ± 0.34 cm | N.S.(0.07132) |
| Cilostazol 30 mg(n = 9) | 7.78 ± 0.67 cm | 1.61 ± 0.38 cm | 9.39 ± 0.67 cm | N.S.(0.109723) |
| Test compound (KC-515)(n = 10) | 5.40 ± 0.91 cm | 1.15 ± 0.33 dm | 6.55 ± 1.10 cm | p ≤ 0.05(2.69368) |

Experiments were started with 10 animals in each group. Two animals died probably because of erroneous administration during experiments, so that the results of the groups treated with vehicle and 30 mg/kg of cilostazol correspond to means of 9 animals.

Treatment with adrenaline+ergotamine induced sloughing, mummification and necrosis in the tail. In this test, the group treated with the test compound (KC-515) showed a decrease in the length of soughing+necrosis with statistically significant difference while the controls treated with cilostazol did not show any effects, revealing that said test compound has the effect of improving peripheral vascular disease in this model.

Industrial Applicability

Pharmaceutical agents comprising a benzopyran or benzoxazine derivative as an active ingredient according to the present invention are useful for the treatment of peripheral vascular disease.

What is claimed is:

1. A method for treating peripheral vascular disease, comprising administering to a patient in need thereof a pharmaceutical composition comprising a therapeutically effective amount of a benzopyran derivative of formula (2):

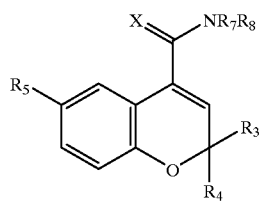

(2)

wherein:
$R_3$ and $R_4$ are identical or different and each represent a lower alkyl group or a substituted lower alkyl group having a halogen atom or a lower alkoxy group as a substituent;
$R_5$ represents a hydrogen atom, a halogen atom, a lower alkyl group, a lower haloalkyl group, a lower alkoxy group, a lower haloalkoxy group, an amino group, an acylamino group, a nitro group, a cyano group, an ester group, a lower alkylsulfonyl group or an arylsulfonyl group;
X represents O or S; and
$R_7$ and $R_8$ are identical or different and each represent a hydrogen atom, a hydroxyl group, a lower alkoxy group, a cyano group, a substituted or unsubstituted amino group, a substituted or unsubstituted and saturated or unsaturated aliphatic hydrocarbon group, a substituted or unsubstituted aryl group, or a substituted or unsubstituted heteroaryl group, or $R_7$ and $R_8$ are joined together to form an optionally substituted heterocycle with a nitrogen atom;
and a pharmaceutically acceptable carrier.

2. The method according to claim 1, wherein $R_5$ represents a lower haloalkyl group and/or $R_7$ and $R_8$ are identical or different and each represent a substituted or unsubstituted and saturated or unsaturated aliphatic hydrocarbon group in the general formula (2).

3. The method according to claim 1, wherein the pharmaceutical composition administered comprises a benzopyran derivative of the general formula (3):

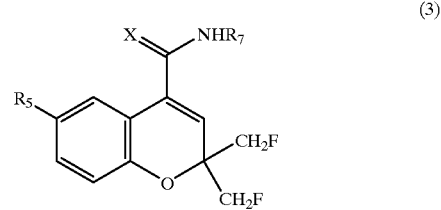

(3)

wherein:
$R_5$ represents a hydrogen atom, a halogen atom, a lower alkyl group, a lower haloalkyl group, a lower alkoxy group, a lower haloalkoxy group, an amino group, an acylamino group, a nitro group, a cyano group, an ester group, a lower alkylsulfonyl group or an arylsulfonyl group;
X represents O or S; and
$R_7$ represents a substituted lower alkyl group;
and a pharmaceutically acceptable carrier.

4. The method according to claim 3, wherein $R_5$ represents a lower haloalkyl group in the general formula (3).

5. The method according to claim 1, wherein the pharmaceutical composition administered comprises a benzopyran derivative of the general formula (4):

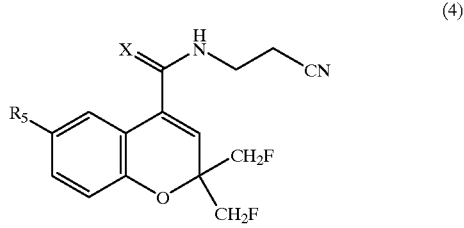

(4)

wherein $R_5$ represents a lower haloalkyl group, and X represents O or S;
and a pharmaceutically acceptable carrier.

6. The method according to claim 1, wherein the pharmaceutical composition administered comprises one or more benzopyran derivatives selected from the group consisting of:

N-(2-cyanoethyl)-6-pentafluoroethyl-2,2-bisfluoromethyl-2H-1-benzopyran-4-carbamide;

N-(2-cyanoethyl)-6-pentafluoroethyl-2,2-bisfluoromethyl-2H-1-benzopyran-4-carbothioamide;

N-(2-cyanoethyl)-2,2-bisfluoromethyl-6-trifluoromethyl-2H-1-benzopyran-4-carbothioamide;

N-(2-cyanoethyl)-2,2-bisfluoromethyl-6-trifluoromethyl-2H-1-benzopyran-4-carbamide;

N-(2-cyanoethyl)-2,2-bisfluoromethyl-6-heptafluoropropyl-2H-1-benzopyran-4-carbamide; and N-(2-cyanoethyl)-2,2-bisfluoromethyl-6-heptafluoropropyl-2H-1-benzopyran-4-carbothioamide;

and a pharmaceutically acceptable carrier.

7. The method according to claim 6, wherein the pharmaceutical composition administered comprises N-(2-cyanoethyl)-6-pentafluoroethyl-2,2-bisfluoromethyl-2H-1-benzopyran-4-carbamide and a pharmaceutically acceptable carrier.

* * * * *

UNITED STATES PATENT AND TRADEMARK OFFICE
CERTIFICATE OF CORRECTION

PATENT NO.   : 6,248,777 B1
DATED        : June 19, 2001
INVENTOR(S)  : Hiroshi Koga et al.

It is certified that error appears in the above-identified patent and that said Letters Patent is hereby corrected as shown below:

<u>Title page, Item [54] and Column 1, lines 1-2,</u>
Delete "REMEDIES FOR PERIPHERAL CIRCULATION DISTURBANCES" and insert therefor -- THERAPEUTIC AGENTS FOR PERIPHERAL VASCULAR DISEASE --

Signed and Sealed this

Sixteenth Day of April, 2002

*Attest:*

*Attesting Officer*

JAMES E. ROGAN
*Director of the United States Patent and Trademark Office*